United States Patent
Warner et al.

[11] Patent Number: 6,159,168
[45] Date of Patent: Dec. 12, 2000

[54] METHOD AND APPARATUS FOR INDUCING AND DETECTING ANATOMIC TORSION

[75] Inventors: Michael John Warner, Johnstown, Pa.; James Allan Mertz, Bricktown, N.J.

[73] Assignee: Cambria Medical Science, Inc., Johnstown, Pa.

[21] Appl. No.: 09/117,821

[22] PCT Filed: Feb. 7, 1997

[86] PCT No.: PCT/US97/01399

§ 371 Date: Jan. 28, 1999

§ 102(e) Date: Jan. 28, 1999

[87] PCT Pub. No.: WO97/28740

PCT Pub. Date: Aug. 14, 1997

Related U.S. Application Data

[60] Provisional application No. 60/011,405, Feb. 9, 1996.

[51] Int. Cl.$^7$ ................................................ A61B 5/103
[52] U.S. Cl. ................................................................ 600/594
[58] Field of Search ................................. 600/587, 594, 600/595

[56] References Cited

U.S. PATENT DOCUMENTS

| | | | |
|---|---|---|---|
| 4,217,912 | 8/1980 | Hubmann et al. | 128/774 |
| 4,235,243 | 11/1980 | Saha | 128/740 |
| 4,250,894 | 2/1981 | Frei et al. | 128/774 |
| 4,297,884 | 11/1981 | Leveque et al. | 73/579 |
| 4,326,416 | 4/1982 | Fredberg | 73/597 |
| 4,416,269 | 11/1983 | Enomoto et al. | 128/41 |
| 4,649,934 | 3/1987 | Fraser et al. | 128/782 |
| 4,655,227 | 4/1987 | Gracovetsky | 128/781 |
| 4,664,130 | 5/1987 | Gracovetsky | 128/781 |
| 4,699,156 | 10/1987 | Gracovetsky | 128/781 |
| 4,754,763 | 7/1988 | Doemland | 128/739 |
| 4,799,498 | 1/1989 | Collier | 128/774 |
| 4,819,753 | 4/1989 | Higo et al. | 128/773 |
| 4,836,215 | 6/1989 | Lee | 128/714 |
| 4,844,085 | 7/1989 | Gattinoni | 128/720 |
| 4,858,126 | 8/1989 | Croce, Jr. | 364/413.02 |
| 4,969,471 | 11/1990 | Daniel et al. | 128/774 |
| 5,050,618 | 9/1991 | Larsen | 128/774 |
| 5,054,502 | 10/1991 | Courage | 128/774 |
| 5,058,600 | 10/1991 | Schechter et al. | 128/716 |
| 5,060,326 | 10/1991 | Oswald | 5/236.1 |
| 5,094,249 | 3/1992 | Marras et al. | 128/781 |
| 5,099,848 | 3/1992 | Parker et al. | 128/661.07 |
| 5,140,994 | 8/1992 | Campbell et al. | 128/782 |
| 5,179,940 | 1/1993 | Barreiro | 128/33 |
| 5,188,121 | 2/1993 | Hanson | 128/781 |
| 5,239,997 | 8/1993 | Guarino et al. | 128/630 |
| 5,337,758 | 8/1994 | Moore et al. | 128/781 |
| 5,373,858 | 12/1994 | Rose et al. | 128/782 |
| 5,398,697 | 3/1995 | Spielman | 128/781 |
| 5,400,800 | 3/1995 | Jain et al. | 128/782 |
| 5,402,781 | 4/1995 | Dimarogonas | 128/653.1 |
| 5,443,079 | 8/1995 | Greenawalt | 128/781 |
| 5,474,086 | 12/1995 | McCormick et al. | 128/782 |
| 5,573,012 | 11/1996 | McEwan | 128/782 |
| 5,588,444 | 12/1996 | Petragallo | 128/782 |
| 5,647,375 | 7/1997 | Farfan de los Godos | 600/594 |

*Primary Examiner*—Cary O'Connor
*Assistant Examiner*—Pamela Wingood
*Attorney, Agent, or Firm*—Webb Ziesenheim Logsdon Orkin & Hanson, P.C.

[57] ABSTRACT

An anatomic torsion monitor includes an examination table (A) equipped with forcibly extendable pads (54, 56) which are utilized to rotationally displace a patient (P) about the patient's transverse axis. A laser (84), or other such pointer, is disposed on a platform (90) which rests across the abdomen of the patient (P) to measure the rotational displacement. The output of the laser (84) is projected onto a scaled chart (100). Clockwise and counterclockwise rotational displacements of the patient (P) as a function of applied forces are obtained by reading the projection of the laser (84) on the scaled chart (100) as the forces are applied and withdrawn. Plotting the rotational displacement versus force on a Cartesian coordinate system produces a continuous, bounded, four quadrant hysteresis loop (116). The data obtained and the hysteresis loop (116) produced therefrom provide a quantitative measure of the motion quality and the motion quantity of the lower back and is subject to detail analytic and medical application.

20 Claims, 4 Drawing Sheets

ROTATIONAL DISPLACEMENT V FORCE (LBS.)

METHOD AND APPARATUS FOR INDUCING AND DETECTING ANATOMIC TORSION

This application claims the benefit of Provisional application Ser. No. 60/011,405 filed Feb. 9, 1996.

1. FIELD OF THE INVENTION

This invention relates to orthopedic tables and, more particularly, to an anatomic torsion monitor for detecting myofascial musculoskeletal elasticity.

2. DESCRIPTION OF THE PRIOR ART

It is well known that the human low back is highly susceptible to disfunction. Some estimates indicate that as much as 20 percent of the population at any one time experiences lower back pain. The annual cost in the United States of this common physical complaint in terms of lost or reduced productivity, and medical costs, is estimated at $100 Billion U.S. dollars yearly. Moreover, low back medical care is typified as having the least return to society for the effort and resources expended.

A common technique utilized by physicians to evaluate low back disfunction is a pelvic roll. In this technique, the physician's fingers contact the Posterior Superior Iliac Spines (PSIS) of a passive supine patient. An anterially directed force applied to one side of the PSIS produces a rotational torque on the lower back. The physician detecting how the PSIS lifts in relation to how much force is applied provides a relative indication of the ability of the lower back to rotate. Normal patients roll with ease from side to side. However, patients with low back dysfunctions roll with less then equal symmetry. Those with moderate to severe dysfunctions roll in one direction with ease while roll in the other direction is met with an abrupt and forceful restriction barrier. Occasionally, the pelvis rolls poorly in both directions. The pelvic roll is a reliable test of low back function since the patient is passive, supine and resting quietly which eliminates the contraction of weight bearing muscles.

The motion of the lumbar vertebrate during the pelvic roll is of particular interest because of facet orientation. Specifically, the bony architecture of the lumbar vertebrate have intervertebratal facets closely oriented to the sagittal plane. These facets function to direct and steer the discs. Movement in the sagittal and coronal planes is well tolerated, while rotation in the transverse plane is extremely limited. Clinically, rotation in the transverse plane is a very sensitive indicator of motion function and disfunction because of its very narrow range of motion arc.

The pelvic roll and other diagnostic techniques for low back problems are subjectively used by physicians in clinical practice. The difficulty in treating patients with low back problems often lies in the inability to make an objective analysis. For example, health care providers who practice manual manipulative medicine, claim to have the ability to make musculoskeletal assessment based on factors of quantity and quality. These practitioners are able to palpate the body and formulate treatment based entirely on the diagnosis obtained by palpitation. Treatment may include manipulation, physical therapy, medicine, surgery or continued observation.

Of particular interest is the assessment of motion quality in terms of tissue response. This is more than a degree of range of motion. Tissue response is how the body reacts to energy transfer. It is the result of a given force supplied, maintained and withdrawn. Terms such as ease of motion and stiffness have been used to describe this dimension of palpitory diagnosis.

Studies have been conducted to define and quantify elasticity, stiffness and motion quality of the human body. These studies, however, have not been able to correlate the mechanical and clinical concepts of elasticity, stiffness and motion quality.

It is therefore an object of the present invention to provide an anatomic torsion monitor that can provide a quantitative measurement of the myofascial-musculoskeletal elasticity. It is an object of the present invention to provide a method for detecting elasticity of muscles, ligaments and myofascial structure in a patient.

SUMMARY OF THE INVENTION

Accordingly, we have invented an anatomic torsion apparatus which includes an examination table for positioning a patient so that the muscles associated with a portion of the anatomy of the patient are relaxed; a rotational torque means which applies a rotational torque to the portion of the anatomy in a first direction and a rotational torque in a second direction opposite the first direction; a rotation displacement measuring means which measures rotational displacement of the anatomy in response to the application or removal of the rotational torque in the first direction and the application removal of the rotational torque in the second direction.

The rotational torque means includes a first pad and a second pad. Each pad is forcibly extendable transverse to a plane of the examination table. The first pad and the second pad are individually extendable. The first pad and the second pad are substantially coplanar with the patient receiving side of the examination table when contracted. The first pad and the second pad are positionable to contact the posterior superior iliac spines of a patient. The forcible extension of the first pad causes rotation of the transverse axis of the patient. The rotation displacement measuring means includes at least one pointer, preferably a laser, positionable to rotate with the anatomy. A detector is positioned to detect the rotational displacement of the pointer as a function of the movement of the projection of the beam of light output by the laser on the detector during rotation of the anatomy.

In one embodiment, the rotational torque means includes a lever attached to each pad. Each lever has a first end attached to a side of the pad opposite the patient receiving side of the examination table. The lever is pivotable about a point between the first end and the second end of the lever. In another embodiment, the rotational torque means includes a linear electric motor, an electric motor and cam arrangement or a hydraulic arrangement for forcibly extending the pad into the patient. The pad, preferably, includes a gimbal ring positioned on the side thereof opposite the patient side. The gimbal ring enables the pad to pivot with respect to the surface of the examination table when the pad is forcibly extended therefrom.

In another embodiment, a method of detecting elasticity of muscles in a patient is provided. In the method, a first force is applied to the patient to cause rotation about the transverse axis of the patient in a first direction. The rotational displacement of the patient about the transverse axis is recorded as a function of the applied first force. The first force is removed and the rotational displacement of the patient in the absence of an applied force is measured. A second force is applied to the patient to cause rotation about the transverse axis of the patient in a second direction opposite the first direction. The rotational displacement of the patient about the transverse axis is recorded as a function of the applied second force. The second force is removed and the rotational displacement of the patient in the absence of applied force is measured.

The method may further include incremental or continuous measurement of the rotational displacement as a function of the application and removal of the first force and the measurement of the rotational displacement as a function of the application and removal of the second force. Moreover, the rotation displacement of the patient in the first direction and the second direction can be determined as a function of time. The rotational displacement of the patient in the first direction and the second direction as a function of time can be Fourier transformed to obtain a spectral analysis thereof.

BRIEF DESCRIPTION OF THE DRAWINGS

FIGS. 8a–8c are top, front and side views of a calibration standard utilized to calibrate the anatomic torsion monitor of FIG. 1.

DESCRIPTION OF THE PREFERRED EMBODIMENTS

Figure 1:
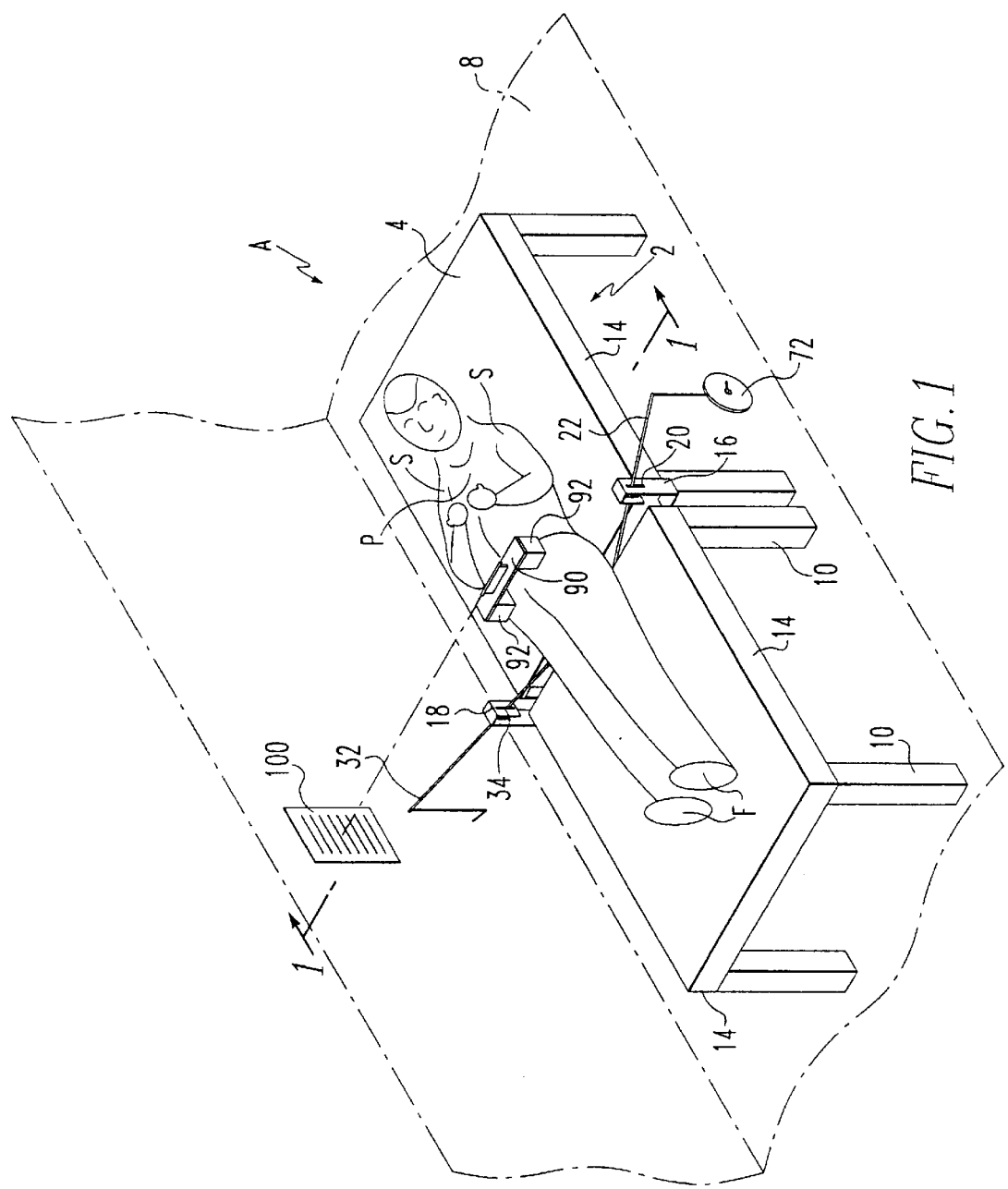
FIG. 1 is a perspective view of an anatomical torsion apparatus with a supine patient disposed thereon.

With reference to FIG. 1, an examination or treatment table A has a substantially planar top 2 having a patient receiving side 4 adapted to receive a patient or subject P to be examined thereon. The top 2 of the examination table 4 is held in spaced relation to a floor 8 by a plurality of legs 10 extending between the floor 8 and a side of the top 2 opposite the patient receiving side 4. The examination table A has a lateral slot 12 formed therein that preferably extends between the sides 14 of the table. A first pivot bracket 16 extends across the slot 12 at one end thereof and a second pivot bracket 18 extends across the slot at the other end thereof. Alternatively, the examination table A is formed from two tables positioned end-to-end and secured together by the first pivot bracket 16 and the second pivot bracket 18 extending between the tables.

Figure 2:
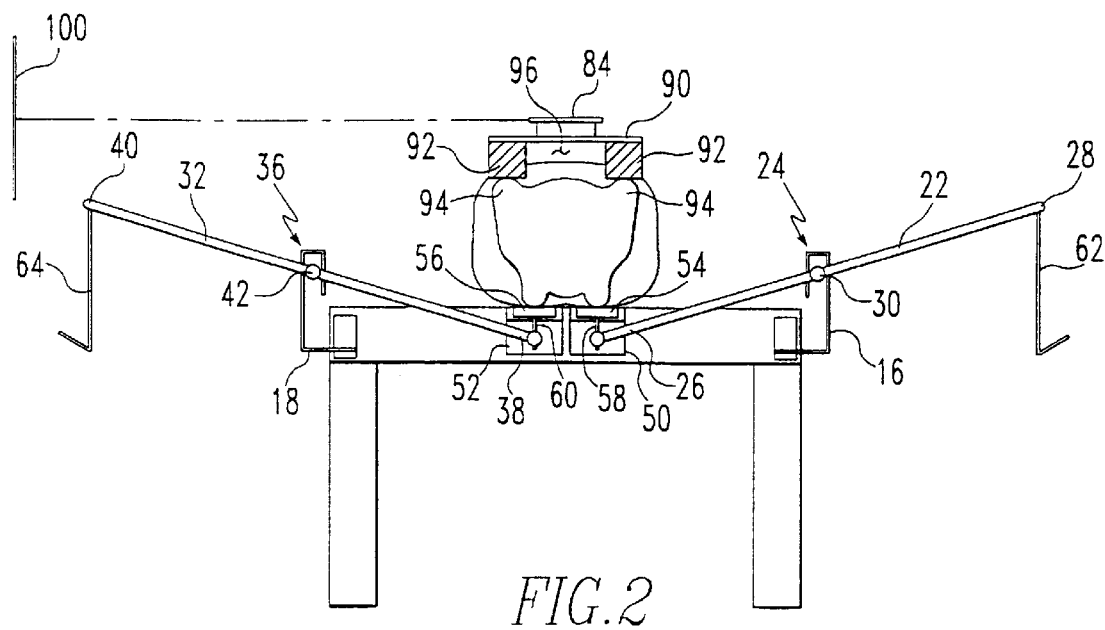
FIG. 2 is a cross section of the apparatus and patient of FIG. 1 taken along section lines 1—1.

With reference to FIG. 2 and with continuing reference to FIG. 1, the first pivot bracket 16 has an aperture 20 formed therein which is adapted to receive a first lever 22. A central part 24 of the first lever, between a first end 26 and a second end 28 thereof, is joined to the first pivot bracket 16 by a first pivot bearing 30 which forms a pivot for the first lever 22. A second lever 32 is received in an aperture 34 formed in the second pivot bracket 18 in a manner similar to the first lever 22 received in the aperture 20 of the first pivot bracket 16. A central part 36 of the second lever 32, between a first end 38 and second end 40 thereof, is joined to the second pivot bracket 18 by a second pivot bearing 42 which forms a pivot for the second lever 32. Preferably, the first pivot bearing 30 and the second pivot bearing 42 are positioned symmetrically on opposite sides of the longitudinal axis of the examination table A and at the same level relative to the patient receiving side 4 of the examination table A.

The first pivot bracket 16 and the second pivot bracket 18 are positioned so that the levers 22, 32 are oriented transverse, and preferably orthogonal, to the longitudinal axis of the examination table A. The first end 26, 38 of each lever 22, 32 is positioned to move vertically through the slot and the second end 28, 40 of each lever 22, 32 extends outward from the sides 14 of the examination table A. Moving the second end 28, 40 of each lever 22, 32 upwardly pivots the lever 22, 32 on its pivot bearing 30, 42 thereby causing the first end 26, 38 thereof to move downwardly. Similarly, moving the second end 28, 40 of each lever 22, 32 downwardly pivots the lever 22, 32 on its pivot bearing 30, 42 so that the first end 26, 38 thereof moves upwardly.

A first support bracket 50 and a second support bracket 52 are positioned in the slot 12. The first support bracket 50 and the second support bracket 52 are adapted to support a first pad 54 and a second pad 56, respectively. The first pad 54 and second pad 56 are supported with their upper surfaces substantially coplanar with the patient receiving side 4 of the examination table A. The first pad 54 and the second pad 56 have a first shaft 58 and a second shaft 60, respectively, extending from lower sides thereof and in a direction opposite the receiving side 4 of the examination table A. The first support bracket 50 and the second support bracket 52 are positionable in the slot 12 to enable the first pad 54 and the second pad 56 to be located at desired locations in the slot, to be described in greater detail hereinafter. When the first pad 54 and the second pad 56 are positioned at the desired locations in the slot 12, e.g., symmetrical with the longitudinal axis of the examination table A, the first support bracket 50 and the second support bracket 52 are fixed in position in the slot 12.

The first shaft 58 is slidably received in the first support bracket 50 so that an upwardly directed force applied to an end of the first shaft 58 opposite the first pad 54 causes the first pad 54 to be forcibly extended transverse to the patient receiving side 4 of the examination table A. Similarly, the second shaft 60 is slidably received in the second support bracket 52 so that an upwardly directed force applied to an end of the second shaft 60 opposite the second pad 56 causes the second pad 56 to be forcibly extended transverse to the patient receiving side 4 of the examination table A. The first pad 54 and the second pad 56 are forcibly extendable transverse to the patient receiving side 4 of the examination table A, preferably, in a plane that extends between the ends of the slot 12 and generally orthogonal to the patient receiving side 4 of the examination table A. When forcibly extended, each pad 54, 56, preferably, converges towards the longitudinal axis of the examination table A at an angle, preferably, between 67 degrees and 69 degrees relative to the patient receiving side 4 of the examination table A. However, other angles of convergence or forcible extension normal to the patient receiving side 4 of the examination table A may also be utilized. The phrase "upwardly directed force" shall be utilized herein to describe the direction of the force applied lengthwise to the shafts 58, 60 which cause the forcible extension of the pads 54, 56.

The first end 26 of the first lever 22 is connected to the end of the first shaft 58 opposite the first pad 54 and the first end 38 of the second lever 32 is connected to the end of the second shaft 60 opposite the second pad 56. The length of the first lever 22 and the length of the second lever 32 are selected so that applying a known downwardly directed force at the second end 28 of the first lever 22 or the second end 40 of the second lever 32 produces a desired upwardly directed force at the corresponding first end 26, 38. The upwardly directed force at the first end 26 of the first lever 22 or the first end 38 of the second lever 32 imparts an upwardly directed driving force to the corresponding first shaft 58 or second shaft 60 which cause the respective first pad 54 or second pad 56 to be forcibly extended transverse to the patient receiving side 4 of the examination table A.

To enable the application of know downwardly directed forces on the levers 22, 32, a first L-shaped hook 62 is connected at its upper end to the second end 28 of the first lever 22 and a second L-shaped hook 64 is connected at its upper end to the second end 40 of the second lever 32. The ends of the hooks 62, 64 opposite the levers 22, 32 are preferably adapted to receive a conventional exercise plate 72. To maintain the exercise plate 72 received on the hooks, the ends of the hooks 62, 64 opposite the levers 22, 32 are preferably tapered upwardly.

Figure 3:
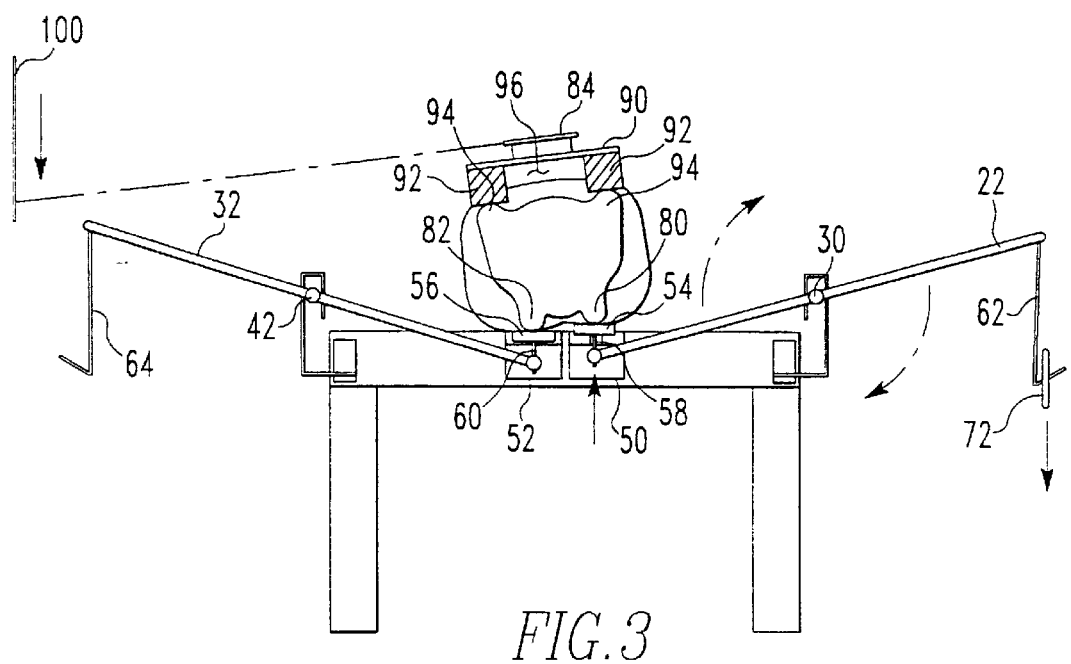
FIG. 3 is the apparatus and patient of FIG. 2 illustrating the lower back of the patient undergoing rotational torque.

With reference to FIG. 3 and with continuing reference to all previous Figs., the first pad 54 and first shaft 58 cause the first lever 22 to experience a force acting to rotate the first lever 22 about the first pivot bearing 30 in a first, counterclockwise, direction. This counterclockwise force is of sufficient extent, in the absence of an exercise plate 72 disposed on the first hook 62, to maintain the first lever 22 in a start position, shown in FIG. 2. Similarly, the second pad 56 and the second shaft 60 cause the second lever 32 to experience a force acting to rotate the second lever 32 in a second, clockwise, direction about the second pivot bearing 42. This clockwise force is of sufficient extent, in the absence of an exercise plate 72 disposed on the second hook 64, to maintain the second lever 32 in a start position. In the start positions, the upper surface of the first pad 54 and the upper surface of the second pad 56 are substantially coplanar with the patient receiving side 4 of the examination table A.

Applying one or more exercise plates 72 to, for example, the first hook 62 causes the first lever 22 to experience a force acting to rotate the first lever in the second, clockwise, direction about the first pivot bearing 30. In response to this clockwise rotation force, the first shaft 58 experiences an upwardly directed force that acts to forcibly extend the first pad 54 transverse to the patient receiving side 4 of the examination table A. Removal of the one or more exercise plates 72 causes the first lever 22 to experience a counterclockwise force acting to return the first lever 22 to its start position. The second lever is similarly rotatable in the counterclockwise and clockwise direction about the second pivot bearing 42 by the respective addition and removal of one or more exercise plates 72 to the second hook 64.

With continuing reference to FIG. 3, the subject or patient P reclines on the examination table A in a supine position. The patient P is positioned on the examination table A so that the Left-Posterior-Superior-Iliac-Spine (LPSIS) 80 and Right-Posterior-Superior-Iliac-Spine (RPSIS) 82 of the patient P are positioned in or above the slot 12. The patient P is preferably positioned on the examination table A so that the sagittal plane of the patient extends parallel with and through the longitudinal axis of the examination table A. The position of the first support bracket 50 and the second support bracket 52 are adjusted in the slot 12 so that the first pad 54 is aligned with, for example, the LPSIS 80 and the second pad 56 is aligned with the RPSIS 82. Reversal of the head and feet position of the patient P on the examination table A will reverse which one of the Posterior-Superior-Iliac-Spine (PSIS) of the patient P, i.e., the LPSIS 80 or the RPSIS 82, is aligned with the first pad 54 and the second pad 56.

As shown in FIG. 3, placement of one or more exercise plates 72 on the first hook 62 causes the first lever 22 to impart an upwardly directed force on the first shaft 58. In response to the upwardly directed force on the first shaft 58, the first pad 54 is forcibly extended into contact with the LPSIS 80 of the patient. The forcible extension of the first pad 54 into the LPSIS 80 of the patient P urges the patient P to rotate about the transverse axis of the patient P in a first, counterclockwise, direction, preferably about the patient's RPSIS 82. During the procedure, the patient P, preferably, rests comfortably and passively on the examination table A and the shoulders S and feet F of the patient remain on the patient receiving side 4 of the examination table A during rotation about the transverse axis of the patient P. Thus, forcible extension of the first pad 54 into the LPSIS 80 of the patient produces a rotational torque on the spine of the patient P in the counterclockwise direction. Similarly, placement of one or more exercise plates 72 on the second hook 64 causes the second lever 32 to impart an upwardly directed force to the second shaft 60 which causes the second pad 56 to be forcibly extended into contact with the RPSIS 82 of the patient P. The second pad 56 forcibly contacting the RPSIS 82 of the patient P produces a rotational torque on the spine of the patient P in the clockwise direction, preferably about the patient's LPSIS 80. Preferably, exercise plates 72 are applied to the first hook 62 independent of the exercise plates being placed on the second hook 64, and vice versa.

To measure the rotational displacement of the spine of the patient P in response to the produced rotational torque, a pointer 84, such as a laser, is positioned adjacent the patient's abdomen in a manner to rotate with the spine of the patient P. The laser 84 produces a output beam of highly focused light that is, preferably, projected orthogonal to the sagittal plane of the patient P.

To ensure the laser 84 rotates with the anatomy being measured, i.e., spine, the laser 84 is secured to a platform 90 which is secured to the patient P. A standoff 92 is disposed on opposite ends of the platform 90 on the side thereof opposite the laser 84. In use, the standoffs 92 are positioned to contact the Anterior-Superior-Iliac Spines (ASIS) 94 of the patient P and the platform 90 is suspended above the patient P between the standoffs 92 thereby forming a gap 96 between the platform and the patient. To ensure the standoffs 92 remain positioned on the ASIS 86 of the patient P, the platform 90 and standoffs 92 are secured to the patient P via, for example, a belt (not shown) surrounding the patient P and the platform 90.

A scaled chart 100 is positioned to receive the beam of light output by the laser 84. The scales on the scaled chart 100 are calibrated so that the projection of the laser 84 on the scaled chart 100 moves thereon in response to rotation of the spine of the patient P by the forcibly extension of the first pad 54 and second pad 56 into the patient P. The movement of the projection of the laser 84 on the scaled chart 100 provides an indication of the rotational displacement of the spine of the patient P.

Figure 4:
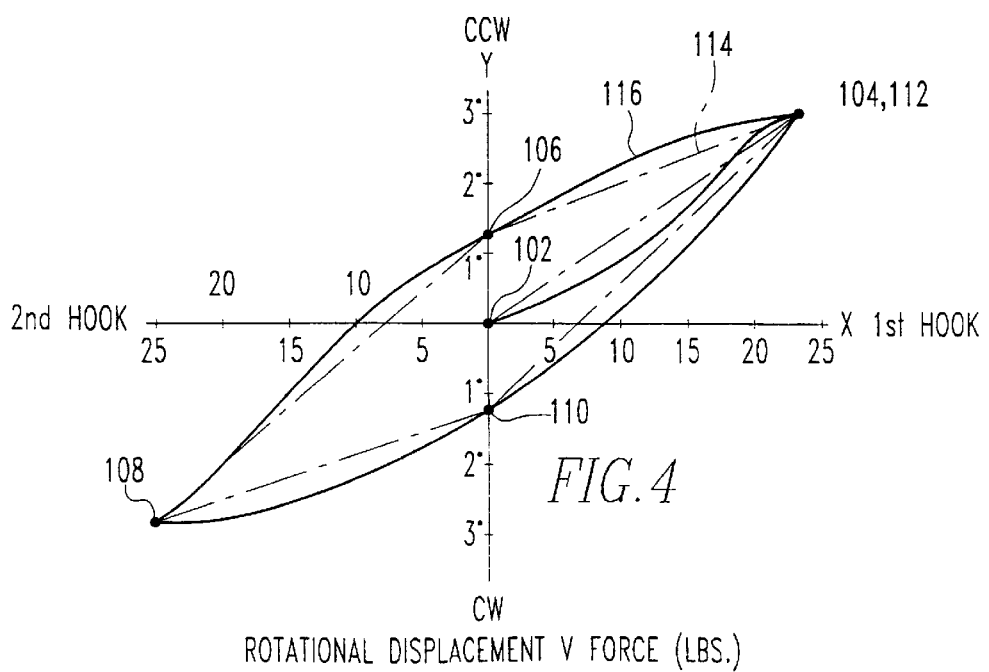
FIG. 4 is a Cartesian coordinate plot of rotational displacement of the lower back of the patient in response to the application of force thereto.

With reference to FIG. 4 and with continuing reference to all previous Figs., in use, the patient P is positioned on the patient receiving side 4 of the examination table A. The LPSIS 80 and RPSIS 82 of the patient P are positioned on the first pad 54 and second pad 56 and the standoffs 92 of the platform 90 supporting the laser 84 are positioned and secured on the ASIS 86 of the patient P. A first reading 102 of the projection of the laser 84 on the chart is recorded in the absence of an exercise plate 72 placed on either the first hook 62 or the second hook 64. This first reading is the "zero" or reference reading. An exercise plate 72 of desired mass is then placed on the first hook 62. In response to the placement of the exercise plate 72 on the first hook 62, the first pad 54 is forcibly extended. This forcible extension of the first pad 54 causes the patient P, and specifically the LPSIS 80 of the patient P, to rotate counterclockwise thereby causing the projection of the laser beam on the scaled chart 100 to move downward. Once the rotation of the patient P stabilizes, the weight of the exercise plate 72 and a second reading 104 of the position of the projection of the laser beam on the scaled chart 100 are recorded. The exercise plate 72 is then removed from the first hook 62. A third reading 106 of the rotational displacement of the patient P is recorded in the absence of an exercise plate 72 on either of the first hook 62 or second hook 64. As shown in FIG. 4, the third reading 106 indicates that the rotational displacement of the patient P after removing the exercise plate 72 from the first hook 62 does not return to the first, zero or reference, reading 102 obtained prior to the application of rotating torque to the patient's P spine. It is believed that this offset between the first reading 102 and the third reading 106 is caused by the lower back, and specifically the patient's lumbar spine, sacroiliac joints and myofascial structures of the lower back, retaining part of the energy introduced by the forcible extension of the first pad 54 into the LPSIS 80 of the patient P.

The exercise plate 72 is next placed on the second hook 64. In response to the placement of the exercise plate 72 on the second hook 64, the second pad 56 is forcibly extended into the RPSIS 82 of the patient P. The forcible extension of the second pad 56 causes the patient P to rotate clockwise thereby causing the projection of the laser beam on the scaled chart 100 to move upward. Once the rotation of the patient stabilizes, the weight of the exercise plate 72 and a fourth reading 108 of the position of the projection of the laser on the scaled chart 100 are recorded. The exercise plate 72 is then removed from the second hook 64 and a fifth reading 110 of the rotational displacement of the patient P in the absence of the exercise plate 72 are recorded. As shown in FIG. 4, the fifth reading 110 indicates that the rotational displacement of the patient after removing the exercise plate from the second hook 64 does not return to the zero reference obtained at the first reading 102 nor does it return to the value of the third reading 106. It is believed that this offset is caused by the lower back retaining part of the energy introduced by the forcible extension of the second pad 56 into the RPSIS 82. The exercise plate 72 is again placed on the first hook 62, which causes the first pad 54 to be forcibly extended. The forcible extension of the first pad 54 causes the patient P to rotate counterclockwise thereby causing the projection of the laser on the scaled chart 100 to move downward. Once the rotation of the patient P stabilizes, the weight of the exercise plate 72 and a sixth reading 112 of the position of the laser on the chart are recorded. The value of the sixth reading 112 is the same or near the value of the second reading 104.

Plotting on a Cartesian coordinate system, the first reading 102 through the sixth reading 112 as a function of the weight of the exercise plate 72, and sequentially joining the first reading 102 through sixth reading 112 with a dashed line results in a first hysteresis loop 114. Plural measurement of the rotational displacement of the spine of the patient P in the counterclockwise and clockwise direction reveals that the rotational displacement as a function of applied weight substantially follows the first hysteresis loop 114.

To obtain a more detailed plot, additional measurements of the rotational displacement of the spine of the patient P as a function of the addition and removal of exercise plates 72 to the first hook 62 and second hook 64 are recorded. For example, the first zero or reference, reading 102 is recorded in the absence of an exercise plate 72 on the hooks 62, 64. An exercise plate 72 weighing, for example, five pounds is placed on the first hook 62. The total weight of the exercise plates 72 on the first hook 62, i.e., five pounds, and the counterclockwise rotational displacement of the spine of the patient P in response thereto are recorded. An additional five pound exercise plate 72 is placed on the first hook 62. The total weight of the exercise plates 72 on the first hook 62, i.e., ten pounds, and the counterclockwise rotational displacement of the spine of the patient P in response thereto are recorded. Additional five pound exercise plates 72 are incrementally placed on the first hook 62. The total weight and counterclockwise rotational displacement of the patient's P spine in response to the incremental addition of each exercise plate 72 are recorded up to a maximum desired weight, e.g., twenty-five pounds, on the first hook 62. The five pound exercise plates 72 then are incrementally removed from the first hook 62 and the total remaining weight and the rotational displacement of the spine of the patient P after removing each exercise plate 72 are recorded. After the last plate 72 has been removed from the first hook 62, the residual counterclockwise rotational displacement of the spine of the patient P is recorded. A five pound exercise plate 72 is then placed on the second hook 64 and the total weight of the exercise plates 72 on the second hook 64, i.e., five pounds, and the clockwise rotational displacement of the spine of the patient P in response thereto are recorded. Another five pound exercise plate 72 is placed on the second hook 64 and the total weight, i.e., ten pounds, and the clockwise rotational displacement of the spine of the patient P in response thereto are recorded. Additional five pound exercise plates 72 are incrementally placed on the second hook 64. The total weight and the clockwise rotational displacement of the spine of the patient P in response to the incremental addition of each exercise plate 72 are recorded up to the maximum desired weight. The five pound exercise plates 72 are then incrementally removed from the second hook 64 and the total remaining weight after removing each exercise plate 72 and the clockwise rotational displacement of the patient P in response thereto are recorded. After the last exercise plate 72 is removed from the second hook 64, the residual clockwise rotational displacement of the spine of the patient P is recorded. The incremental placement of five pound exercise plates 72 on the first hook 62 and the recording of the total weight and the counterclockwise rotational displacement of the spine of the patient P for the incremental addition of each exercise plate 72 is repeated until the desired maximum weight has again been placed on the first hook 62. Thereafter, the exercise plates 72 are removed from the hooks 62, 64.

A plot is formed on a Cartesian coordinate system of the rotational displacements of the spine of the patient P as a function of the incremental total weight added and removed from the first hook 62 and the second hook 64. Specifically, the total weight on the first hook 62 is represented on the positive abscissa, the counterclockwise rotational displacement is represented on positive ordinate, the total weight on the second hook is represented on the negative abscissa and the clockwise rotational displacement is represented on the negative ordinate. For a patient P with a healthy lower back, the plot of rotational displacement versus total weight results in a second hysteresis loop 116.

The actual shape of the hysteresis loops 114, 116 for healthy lower backs may vary from patient to patient. However, the general shape of these hysteresis loops 114, 116 will be similar. For patient's with unhealthy lower backs, the hysteresis loops 114, 116 will be perceptibly distorted in one or more quadrants of the Cartesian coordinate system. Moreover, as a patient P recovers from a lower back injury, the hysteresis loops will transition from a distorted hysteresis loop toward, for example, the second hysteresis loop 116.

Figure 5:
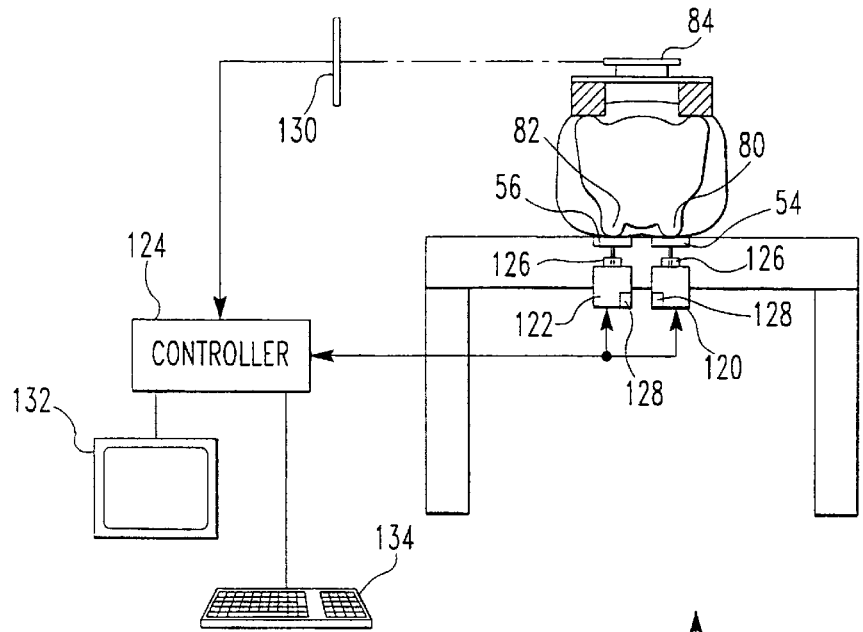
FIG. 5 is a cross section of another embodiment of the anatomic torsion apparatus.

With reference to FIG. 5, a first drive 120 and a second drive 122, such as a first and second motor/cam arrangement, a first and second first linear motor or a first and second hydraulic arrangement, are utilized to controllably impart an upwardly directed force to the first pad 54 and the second pad 56, respectively. Specifically, a controller 124 outputs to the first drive 120 and the second drive 122 individual control and/or drive signals. In response to receiving the control signals, each drive 120, 122 imparts to its corresponding pad 54, 56 an upwardly extending force corresponding to the received control signals. By adjusting the control signals to each drive 120, 122, the extent of the upwardly extending force imparted to each pad 54, 56 can be controlled. To accurately measure the extent of the applied upwardly extending force, each drive 120, 122; pad 54, 56 or shaft 58, 60 may be equipped with a corresponding force sensor 126, such as a load cell, which converts the upwardly extending force of the pad coacting with the spine of the patient P into an electrical signal detectable by the controller 124. The controller 124 utilizes the electrical signal output by the force sensors 126 in a feedback mode to determine if the applied control signal is causing the corresponding drive 120, 122 to produce the desired extent of upwardly extending force. The controller 124 also utilizes the electrical signals output by the force sensors 126 to detect if insufficient force is being detected, as would occur if the patient P shifts off a pad 54, 56. Each drive 120, 122 each may also include a position detector 128, such as an encoder or a resolver, which detects the distance the pad 54, 56 has traveled from the patient receiving side 4 of the examination table A. The position detectors 128 can be utilized, without limitation, to limit the extent of travel of the pads 54, 56. The position detectors 128 can also be utilized to obtain an indication of the rotational displacement of the patient P.

An optical array 130, formed from a plurality of optical pick-ups, such as photo-diodes, is positioned in the projected light path output by the laser 84. Each optical pick-up is adapted to produce an electrically detectable signal in response to the receipt of light from the laser 84. The optical array 130 is positioned in the path of light output by the laser 84 and is adapted to detect and provide an indication of the position of light from the laser 84 impinging thereon. The optical array 130 is suitably placed relative to the laser 84 to enable accurate detection of the movement of the projection of the beam of light from the laser 84 as a function of the rotational displacement of the patient P. The optical array 130 is connected to the controller 124 which includes suitable circuitry to enable the detection of which one, or ones, of the optical pick-ups in the optical array 130 are producing an electrically detectable signal in response to the receipt of light from the laser 84.

The controller 124, preferably, has a CRT 132 and a keyboard 134 attached thereto for enabling a operator to interface therewith. The controller 124 includes suitable operating software and hardware for controlling the operation of the drives 120, 122, the receipt electrically detectable signals from the optical array 130, the generation of images on the CRT 132 and the receipt of inputs from the keyboard 134.

In use, the controller 124 coordinates the operation of the drives 120, 122 and the optical array 130 to obtain readings of the rotational displacement of the spine of the patient P as a function of force applied to the LPSIS 80 and RPSIS 82. Specifically, once the PSIS of the patient P are positioned on the first pad 54 and second pad 56, the controller 124 samples the optical array 130 to determine which one, or ones, of the optical pick-ups is receiving light from the laser 84. The controller 124 increments the upwardly directed force applied to, for example, the LPSIS 80 of the patient P by the first drive 120 and detects the rotational displacement of the patient P in response thereto by sampling the optical array 130 after each increment of upwardly applied force. The upwardly directed force applied by the first drive 120 is in the absence of an upwardly directed force applied by the second drive 122. When the maximum desired upwardly directed force has been applied by the first drive 120, the controller 124 decrements the upwardly directed force and detects the return rotational displacement of the patient P by sampling the optical array 130 after each such decrement. The controller 124 then increments increases the upwardly applied force applied to the RPSIS 82 of the patient P by the second drive 122 and detects the rotational displacement of the spine of the patient P in response thereto by sampling the optical array 130 after each increment of upwardly applied force. The upwardly directed force applied by the second drive 122 is in the absence of an upwardly directed force being applied by the first drive 120. When the maximum desired upwardly directed force has been applied by the second drive 122, the controller 124 decrements the upwardly applied force and detects the return rotational displacement of the RPSIS 82 of the patient P by sampling the optical array 130 after each such decrement. The increment and decrement of upwardly applied force by the first drive 120 and the second drive 122 and the detection of the rotational displacement of the spine of the patient P in response thereto can continue until sufficient data regarding the rotational displacement as a function of the upwardly directed force has been accumulated.

The controller 124 preferably includes software to generate from the accumulated data, a hysteresis loop, e.g., the second hysteresis loop 116 in FIG. 4, for the patient P. This hysteresis loop can be displayed on the CRT 132 or printed on a printer (not shown). The controller 124 may also include suitable mass storage (not shown) for storing the data regarding the rotational displacement as a function of upwardly applied force for subsequent retrieval and analysis. Such analysis may include, without limitation, the generation of additional hysteresis loops or the Fourier Transforming of the data into the frequency domain for spectral analysis.

To enable the application of forces in a desired direction while the patient P is being rotated, each pad 54, 56 is preferably attached to a shaft 58, 60 via a gimbal ring 136. The gimbal rings 136 enable the pads 54, 56 to maintain a desired direction of force on the patient P during the forcible extension of the pads 54, 56.

Rotational displacement of the patient P three degrees clockwise and three degrees counterclockwise, for a total of six degrees, is believed to provide sufficient diagnostically useful information about the lower back. It is to be appreciated, however, that additional degrees of clockwise and counterclockwise rotational displacement can also be utilized.

Figure 7:
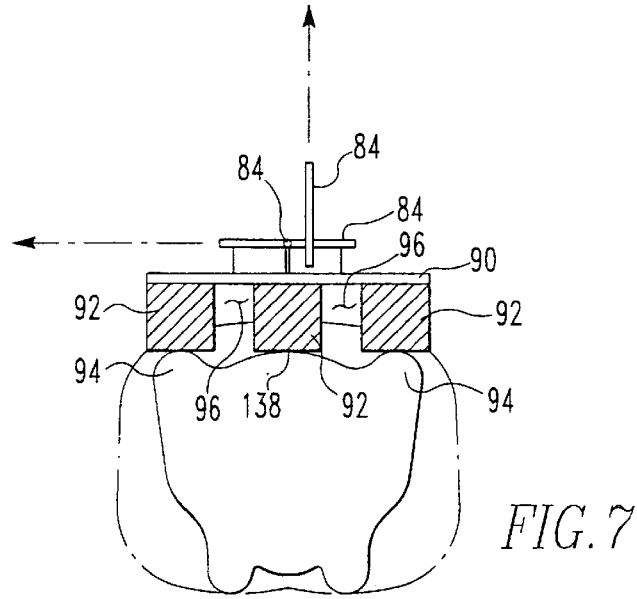
FIG. 7 is a cross section of the platform and patient of FIG. 6 taken across section lines 3—3.
Figure 6:
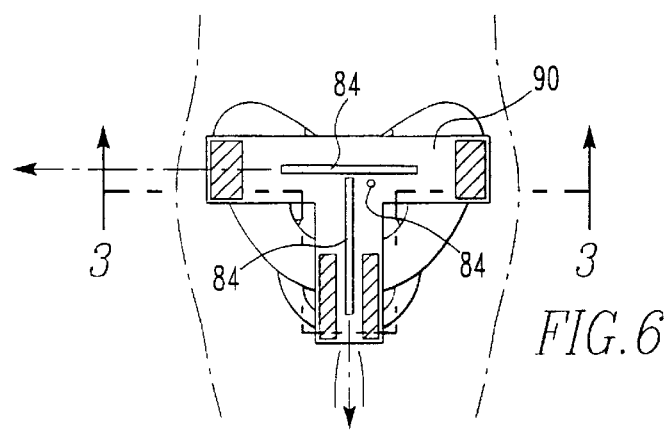
FIG. 6 is an embodiment of a platform for supporting a plurality of lasers that are utilized to detect the rotational displacement of the lower back of the patient in a plurality of orthogonal planes.

With reference to FIGS. 6 and 7, the platform 90 is adapted to support two or more lasers 84 orthogonal to each other. Standoffs 92 are disposed on the side of the platform 90 opposite the lasers 84 and are positioned to contact the ASIS 94 and the pubic bone 138 of the patient P. The standoffs 92 are of sufficient height so that the platform 90 bridges the standoffs 90 and forms the gap 96 with the abdomen of the patient P. The standoffs 92 and platform 90, including lasers 84, are positioned on the patient P and secured to the patient utilizing, for example, a belt. The output of each laser 84 is projected onto a scaled chart 100 or an optical array 130. The rotational displacement of the spine of the patient P as a function of applied force is then determined in the above described manner. It is believed that the detection of rotational displacement of the lower back of the patient P in more than one plane will provide useful diagnostic information.

Figure 8B:
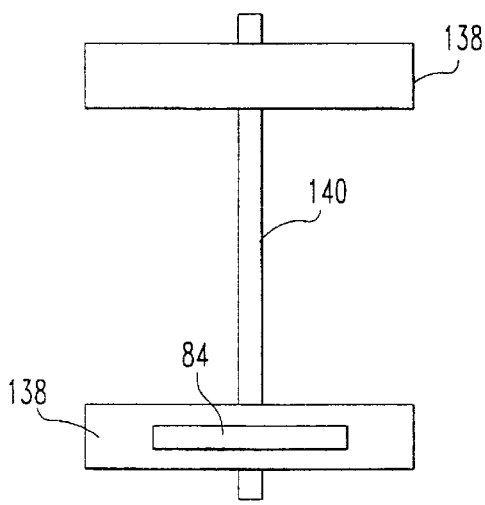
Figure 8B:
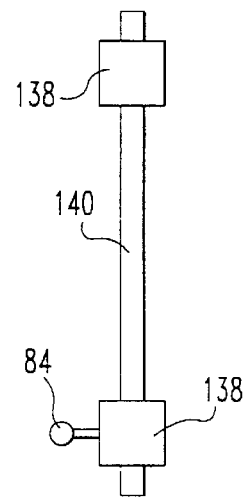

With reference to FIGS. 8(a)–8(c), a pair of non-elastic metal blocks 138 are separated by and secured to a calibration rod 140 having a desired elasticity. To calibrate the examination table A one of the blocks 138 is positioned between the first pad 54 and second pad 56. The other of the blocks 138 is positioned on the patient receiving side 4 of the examination table A and is, preferably, secured thereto. The blocks 138 are preferably positioned on the table A so that the longitudinal axis of the calibration rod 140 is positioned above and in alignment with the longitudinal axis of the examination table A. A laser 84 is positioned on the one of the blocks 138 positioned between the first pad 54 and second pad 56. The laser 84 is projected onto a scaled chart 100 or the optical array 130. Clockwise and counterclockwise rotational torques are incrementally applied to the calibration bar 140 by forcibly extending the first pad 54 and then the second pad 56 into the one of the blocks 138 positioned between the pads 54, 56. The projection of the laser 84 on the chart 100 or optical array 130 in response to the forcible extension is detected for each increment. A plot on a Cartesian coordinate system of clockwise displacement and counterclockwise displacement as a function of applied force reveals a substantially linear relationship therebetween. This substantially linear relationship indicates that the examination table A contributes minimal or predictable artifacts to the hysteresis loops, e.g., 114, 116.

It can be seen from the foregoing that the present invention is an anatomic torsion monitor that can provide a quantitative measurement of the myofascial-musculoskeletal elasticity. The present invention also provides a method for detecting elasticity of muscles, ligaments and myofascial structure in a patient.

It is believed that the above-described invention, and specifically the embodiment shown in FIG. 5, can be connected to a central data collection computer. Such central data collection computer can be utilized to obtain data regarding rotational displacement versus force for a plurality of patients from a plurality of anatomic torsion monitors. This data can then be utilized by the central data collection computer for correlated purposes.

The invention has been described with reference to the preferred embodiments. Obvious modifications and alterations will occur to others upon reading and understanding the preceding detailed description. It is intended that the invention be construed as including all such modifications and alterations, insofar as they come within the scope of the appended claims or the equivalents thereof.

We claim:

1. An anatomic torsion apparatus for detecting myofascial-musculoskeletal elasticity, the torsion apparatus comprising:

an examination table for positioning a patient so that the muscles associated with a portion of the anatomy of the patient are relaxed;

a rotational torque means for applying to the portion of the anatomy a rotational torque in a first direction and a rotational torque in a second direction opposite the first direction, with the rotational torque means including a first pad forcibly extendable transverse to a plane of the examination table and a second pad forcibly extendable transverse to the plane of the examination table; and a rotational displacement measuring means for measuring a rotational displacement of the portion of the anatomy in response to the application and removal of the rotational torque in the first direction and the application and removal of the rotational torque in the second direction, wherein:

one of the first pad and the second pad is individually forcibly extended in the absence of the other of the first pad and the second pad being forcibly extended, and vice versa, whereby the rotational torque in the first direction is applied in the absence of rotational torque in the second direction and rotational torque in the second direction is applied in the absence of rotational torque in the first direction; and the first pad and the second pad, when contracted, are substantially coplanar with the plane of the examination table.

2. The anatomic torsion apparatus as set forth in claim 1, wherein the rotational torque in one of the first direction and the second direction is applied transverse to the longitudinal axis of the portion of the anatomy.

3. The anatomic torsion apparatus as set forth in claim 1, wherein the portion of the anatomy is a spine of a patient including associated structure.

4. The anatomic torsion apparatus as set forth in claim 1, wherein the first pad and the second pad are positionable to contact the posterior-superior iliac spines.

5. The anatomic torsion apparatus as set forth in claim 1, wherein the forcible extension of one of the first pad and the second pad causes rotation about the transverse axis of the patient.

6. The anatomic torsion apparatus as set forth in claim 1, further including a calibration means positioned between the rotational torque means and the rotational displacement measuring means for causing the rotational displacement measuring means to undergo a known rotational displacement in response to the application by the rotational torque means of a known rotational torque to the calibration means.

7. The anatomic torsion apparatus as set forth in claim 1, wherein the rotational displacement measuring means includes:

a pointer positionable to rotate with the anatomy and point one of (i) transverse to a longitudinal axis of the anatomy and (ii) parallel with a longitudinal axis of the anatomy; and a detector which detects rotational displacement of the pointer during rotation of the anatomy.

8. The anatomic torsion apparatus as set forth in claim 7, wherein the pointer is a laser and the detector is one of a scaled chart and an optical array positioned to receive an output of the laser.

9. The anatomic torsion apparatus as set forth in claim 7, further including a platform positionable on the anatomy and supporting the pointer during rotation of the anatomy.

10. The anatomic torsion apparatus as set forth in claim 9, further including a standoff disposed on opposite ends of the platform on the side of the platform opposite the pointer, wherein the portion of the anatomy is a spine of a patient, and wherein the sides of each standoff opposite the platform are positionable on the anterior-superior iliac spines.

11. The anatomic torsion apparatus as set forth in claim 10, wherein the platform and the anatomy form a gap therebetween.

12. An examination table for detecting elasticity of muscles, the examination table comprising:
 a table having a receiving side for receiving a supine patient thereon;
 a pair of pads spaced from each other and positioned laterally to a longitudinal axis of the table, with each pad having an upper surface positionable substantially coplanar with the receiving side of the table; and
 a drive means for forcibly extending one pad away from the receiving side of the table in the absence of forcible extension of the other pad, and vice versa, the upper surface of the one pad remaining substantially coplanar with the receiving side of the table when the other pad is forcibly extended and with the other pad remaining substantially coplanar with the receiving side of the table when the one pad is forcibly extended, wherein:
  the patient is receivable on the receiving side of the table with the one pad contacting a right-posterior-superior iliac spine (RPSIS) of the patient and with the other pad contacting a left-posterior-superior iliac spine (LPSIS) of the patient;
  the forcible extension of the one pad causes the patient to rotate about a transverse axis of the patient in a first direction, with the RPSIS of the patient moving away from the receiving side of the table; and
  the forcible extension of the other pad causes the patient to rotate about the transverse axis of the patient in a second direction opposite the first direction, with the LPSIS of the patient moving away from the receiving side of the table.

13. The examination table as set forth in claim 12, wherein:
 the drive means includes one lever having a first end attached to a side of the one pad opposite the receiving side of the table and pivotable about a point between the first end and a second end thereof;
 the first end of one lever experiences an upward force in response to the application of a downward force at the second end of the one lever;
 the drive means includes another lever having a first end attached to a side of the other pad opposite the receiving side of the table and pivotable about a point between the first end and second end thereof; and
 the first end of the other lever experiences an upward force in response to the application of a downward force at the second end of the other lever.

14. The examination table as set forth in claim 12, wherein the drive means includes one of:
 (i) an electric motor and cam;
 (ii) a linear electric motor; and
 (iii) a hydraulic apparatus.

15. The examination table as set forth in claim 12, further including:
 a controller;
 a laser; and
 an optical array, wherein:
  the laser is secured to an anterior-superior iliac spine of the patient;
  the optical array is positioned to receive light output by the laser; and
  the controller coordinates the operation of the drive means and the optical array to obtain readings from the optical array indicative of the rotational displacement of the patient as a function of the forcible extension of the one pad or the other pad.

16. The examination table as set forth in claim 12, further including a gimbal ring connected between the one pad and the drive means, the gimbal ring enabling the one pad to pivot with respect to the receiving side of the table when the one pad is forcibly extended therefrom.

17. A method of detecting the elasticity of muscles in a patient, the method comprising the steps of:
 applying to a supine patient received on a planar surface a first force which causes rotation about the patient's transverse axis in a first direction;
 measuring the rotational displacement of the patient about the transverse axis as a function of the applied first force;
 removing the first force;
 measuring the rotational displacement of the patient in the absence of an applied force;
 applying to the supine patient a second force which causes rotation about the patient's transverse axis in a second direction opposite the first direction;
 measuring the rotational displacement of the patient about the transverse axis as a function of the applied second force;
 removing the second force; and
 measuring the rotational displacement of the patient in the absence of an applied force.

18. The method as set forth in claim 17, further including the step of:
 forming a plot of the measured rotational displacement as a function of the first force and the measured rotational displacement as a function of the second force.

19. The method as set forth in claim 17, further including the step of:
 determining the rotational displacement of the patient in the first direction and the second direction as a function of time.

20. The method as set forth in claim 19, further including the step of:
 Fourier transforming the rotational displacement of the patient in the first direction and the second direction as a function of time.

* * * * *